United States Patent
Ditzel et al.

(10) Patent No.: US 9,598,347 B2
(45) Date of Patent: Mar. 21, 2017

(54) CARBONYLATION PROCESS

(71) Applicant: BP Chemicals Limited, Middlesex (GB)

(72) Inventors: Evert Jan Ditzel, East Yorkshire (GB); Bogdan Costin Gagea, Berkshire (GB); David John Law, East Yorkshire (GB); John Glenn Sunley, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 14/773,220

(22) PCT Filed: Mar. 6, 2014

(86) PCT No.: PCT/EP2014/054395
§ 371 (c)(1),
(2) Date: Sep. 4, 2015

(87) PCT Pub. No.: WO2014/135662
PCT Pub. Date: Sep. 12, 2014

(65) Prior Publication Data
US 2016/0009629 A1    Jan. 14, 2016

(30) Foreign Application Priority Data

Mar. 8, 2013  (EP) .................................. 13158469

(51) Int. Cl.
| | | |
|---|---|---|
| *C07C 67/36* | (2006.01) | |
| *C07C 67/37* | (2006.01) | |
| *B01J 37/08* | (2006.01) | |
| *B01J 29/06* | (2006.01) | |
| *B01J 29/18* | (2006.01) | |
| *B01J 29/24* | (2006.01) | |
| *B01J 29/65* | (2006.01) | |
| *B01J 29/70* | (2006.01) | |
| *B01J 29/87* | (2006.01) | |
| *B01J 37/00* | (2006.01) | |
| *C07C 51/09* | (2006.01) | |

(52) U.S. Cl.
CPC ............... *C07C 67/37* (2013.01); *B01J 29/06* (2013.01); *B01J 29/18* (2013.01); *B01J 29/185* (2013.01); *B01J 29/24* (2013.01); *B01J 29/65* (2013.01); *B01J 29/70* (2013.01); *B01J 29/7015* (2013.01); *B01J 29/7026* (2013.01); *B01J 29/87* (2013.01); *B01J 37/0009* (2013.01); *B01J 37/0018* (2013.01); *B01J 37/08* (2013.01); *C07C 51/09* (2013.01); *B01J 2229/14* (2013.01); *B01J 2229/18* (2013.01); *B01J 2229/42* (2013.01)

(58) Field of Classification Search
CPC ......... C07C 67/37; C07C 69/14; C07C 51/09; B01J 2229/14; B01J 2229/18; B01J 2229/42; B01J 29/06; B01J 29/18; B01J 29/185; B01J 29/24; B01J 29/65; B01J 29/70; B01J 29/7015; B01J 29/7026; B01J 29/87; B01J 37/0009; B01J 37/0018; B01J 37/08
See application file for complete search history.

(56) References Cited

U.S. PATENT DOCUMENTS

| | | | |
|---|---|---|---|
| 4,612,387 A | | 9/1986 | Feitler |
| 5,164,170 A | * | 11/1992 | Rubin .................. B01J 29/7007 423/709 |
| 7,465,822 B2 | | 12/2008 | Cheung et al. |
| 2007/0238897 A1 | * | 10/2007 | Cheung .................. C07C 51/09 560/232 |

FOREIGN PATENT DOCUMENTS

| | | | |
|---|---|---|---|
| EP | 0 018 090 A1 | | 10/1980 |
| EP | 1985606 | * | 10/2008 |
| EP | 2 189 215 A1 | | 5/2010 |
| EP | 2 199 272 A1 | | 6/2010 |
| EP | 2198963 | * | 6/2010 |
| EP | 2199272 | * | 6/2010 |
| WO | WO2005105720 | * | 2/2005 |
| WO | WO 2005/105720 A1 | | 11/2005 |
| WO | WO 2006/121778 A1 | | 11/2006 |
| WO | WO 2008/016423 A1 | | 2/2008 |
| WO | WO 2008/132438 A1 | | 11/2008 |
| WO | WO2008132438 | * | 11/2008 |
| WO | WO2010058149 | * | 5/2010 |

OTHER PUBLICATIONS

Yaripour, F., et al; "Catalytic dehydration of methanol to dimethyl ether (DME) over solid-acid catalysts"; *Catalysis Communications*, Elsevier Science, Amsterdam, vol. 6, No. 2, pp. 147-152 (2005).
Yaripour, F., et al; "Catalysis Communications", *Elsevier Science*, Amsterdam, vol. 6, No. 2, pp. 147-152 (2005).

* cited by examiner

*Primary Examiner* — Yevegeny Valenrod
*Assistant Examiner* — Blaine G Doletski
(74) *Attorney, Agent, or Firm* — Nixon & Vanderhye P.C.

(57) ABSTRACT

Process for the carbonylation of dimethyl ether with carbon monoxide in the presence of a catalyst to produce methyl acetate reaction product. The carbonylation process is conducted in the presence of hydrogen at a molar ratio of hydrogen to carbon monoxide of greater than 1 and the catalyst is a mordenite zeolite prepared from a synthesis mixture comprising at least one organic structure directing agent.

35 Claims, 1 Drawing Sheet

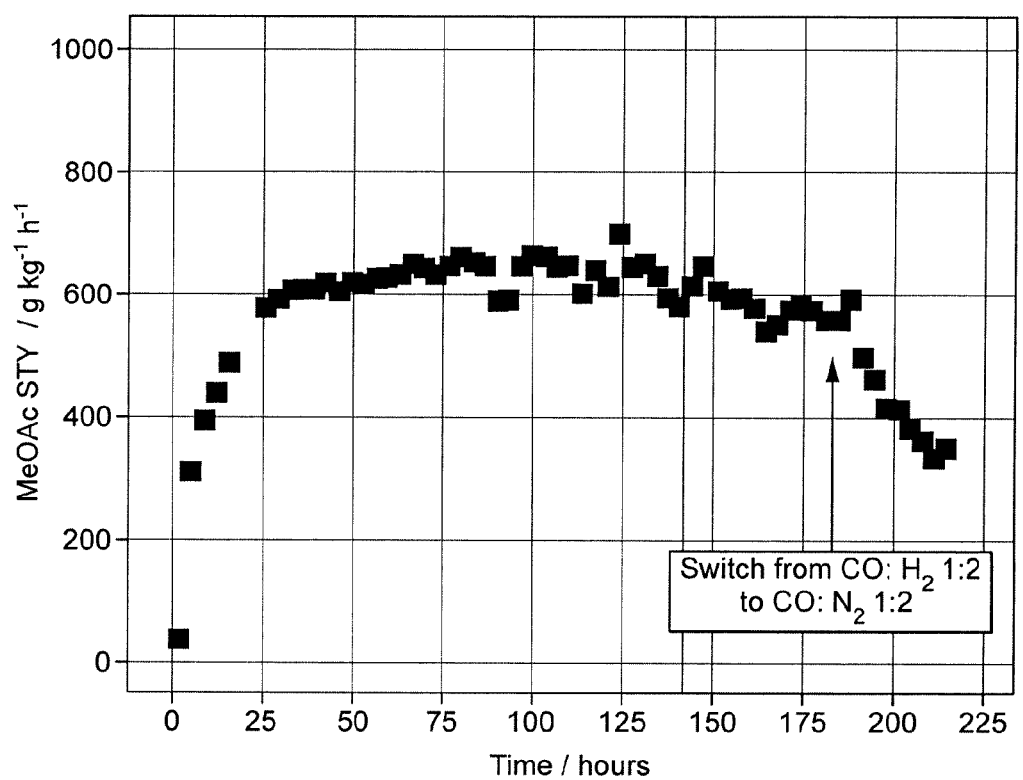

CARBONYLATION PROCESS

This application is the U.S. national phase of International Application No. PCT/EP2014/054395 filed Mar. 6, 2014 which designated the U.S. and claims priority to European Patent Application No. 13158469.0 filed Mar. 8, 2013, the entire contents of each of which are hereby incorporated by reference.

This invention relates to a process for the carbonylation of dimethyl ether with carbon monoxide in the presence of a zeolite catalyst and hydrogen to prepare methyl acetate. In particular the invention relates to a process for the carbonylation of dimethyl ether with carbon monoxide in the presence of hydrogen at a molar ratio of hydrogen to carbon monoxide of at least 1 and a zeolite catalyst which is prepared from a synthesis mixture comprising an organic structure directing agent.

BACKGROUND OF THE INVENTION

Crystalline aluminosilicate zeolites are known to catalyse various chemical conversion processes including the carbonylation of dimethyl ether to produce methyl acetate. Such carbonylation processes may be conducted in the presence of hydrogen but are typically conducted with an excess amount of carbon monoxide such as described in, for example EP 2189215 and EP 2199272.

EP 2189215 describes processes for the production of acetic acid and/or methyl acetate products by carbonylating dimethyl ether or methanol with carbon monoxide in the presence of a bound hydrogen form mordenite catalyst and optionally hydrogen.

EP 2199272 describes processes for the carbonylation of dimethyl ether with carbon monoxide in the presence of a mordenite catalyst, hydrogen and additional methyl acetate in which the carbon monoxide is utilised in a molar excess compared to hydrogen.

In general, zeolites are prepared by a procedure which involves crystallizing the zeolite structure from aqueous synthesis mixtures comprising sources of appropriate oxides, such as silica and alumina. Structure directing agents influence the formation of channels or tunnel like structures (a microporous structure) within a zeolite and may also be included in the synthesis mixture. Structure directing agents may be inorganic or they may be organic. Structure directing agents are removed from the formed zeolites by a variety of methods. Inorganic structure directing agents are generally removed by ion-exchange methods whereas organic structure directing agents may be removed by calcining at high temperature. Zeolites produced in this manner have been found to be useful as catalysts, as described, for example in WO 2005/105720.

WO 2005/105720 describes a carbonylation process for the carbonylation of aliphatic alcohols and/or reactive derivatives thereof in the presence of a mordenite catalyst which has, in addition to aluminium and silicon, one or more gallium, boron and iron as framework elements and which catalyst is also loaded with copper, nickel, iridium, rhodium or cobalt. The preparation of gallium mordenite is described in which tetraethyl ammonium bromide is used as an organic template and which template is removed by calcining at 550° C. prior to use in the carbonylation of methanol with carbon monoxide.

U.S. Pat. No. 7,465,822 describes a process for the carbonylation of a lower alkyl ether with carbon monoxide in the presence of a zeolite catalyst. It is disclosed that in the synthesis of the zeolite, an organic structure directing agent may be included in the reaction mixture which mixture is subsequently crystallised and calcined at high temperatures.

In general it is less costly and therefore desirable to commercially manufacture zeolites without the use of organic structure directing agents. However, an important aspect of any catalytic process is the activity of a catalyst when exposed to the desired process conditions. The improvement of catalytic performance in carbonylation reactions is a continuous objective of process and catalyst development research.

Mixtures of carbon monoxide and hydrogen (generally referred to as synthesis gas) are produced commercially and are readily available. Typically, synthesis gas mixtures are hydrogen-rich, that is hydrogen is present in such mixtures in at least an equimolar and generally in an excess molar ratio to carbon monoxide. In carbonylation processes the use of such hydrogen-rich feeds results in less space for carbon monoxide in the reactor, leading to reduced carbon monoxide partial pressures and reduced rates of reaction. Consequently, synthesis gas mixtures are processed to separate out the components carbon monoxide and hydrogen, for example by expensive cryogenic techniques. However, to avoid such costly separation of carbon monoxide from hydrogen it would be advantageous to be able to utilise synthesis gas mixtures in zeolite catalysed carbonylation processes without the need to reduce the hydrogen:carbon monoxide molar ratio thereof. Thus, a problem which exists in zeolite catalysed carbonylation processes is that in order to operate such carbonylation processes under hydrogen-rich conditions, and in particular under hydrogen-rich conditions throughout the process, necessitates an increase in the activity requirements of a zeolite catalyst.

SUMMARY OF THE INVENTION

Applicant has now found that materially enhanced activity for the carbonylation of dimethyl ether with carbon monoxide in the presence of hydrogen, and in particular in the presence of an equimolar or molar excess of hydrogen, can be achieved by utilising zeolites prepared from synthesis mixtures comprising an organic structure directing agent. In particular, Applicant has found that zeolites prepared using an organic structure directing agent provide improved catalytic performance in carbonylation processes carried out in the presence of an equimolar or excess amount of hydrogen compared to equivalent zeolites which have been prepared without the aid of an organic structure directing agent. Without wishing to be bound by theory, it may be speculated that the organic structure directing agent serves to control the size or other characteristics such as shape of the zeolite crystals formed during crystallisation such that the resultant zeolite possesses smaller average crystal sizes. It may also be speculated that the organic structure directing agent functions to increase the relative amount of alkali/alkaline earth metal cations in those channels of the zeolite where the carbonylation reaction takes place.

Accordingly, the present invention provides a process for the carbonylation of dimethyl ether with carbon monoxide in the presence of a catalyst to produce methyl acetate reaction product which carbonylation process is conducted in the presence of hydrogen at a molar ratio of hydrogen to carbon monoxide of at least 1 and the catalyst is a zeolite prepared from a synthesis mixture comprising at least one organic structure directing agent.

The present invention also provides a process for improving the performance of a zeolite catalyst in a process for the carbonylation of dimethyl ether with carbon monoxide in the presence of the catalyst to produce methyl acetate reaction product which carbonylation process is carried out in the presence of hydrogen at a molar ratio of hydrogen to carbon monoxide of at least 1 wherein the zeolite is prepared from a synthesis mixture comprising at least one organic structure directing agent.

The present invention further provides a zeolite catalyst which provides improved catalytic performance for the carbonylation of dimethyl ether with carbon monoxide in the presence of the catalyst to produce methyl acetate reaction product which carbonylation is carried out in the presence of hydrogen at a molar ratio of hydrogen to carbon monoxide of at least 1 and the catalyst is a zeolite prepared from a synthesis mixture comprising at least one organic structure directing agent.

In some or all embodiments of the present invention the synthesis mixture for preparing the zeolite further comprises a source of silica, a source of alumina, a source of alkali or alkaline earth metal and water.

Thus, in some or all embodiments of the present invention there is provided a process for the carbonylation of dimethyl ether with carbon monoxide in the presence of a catalyst to produce methyl acetate reaction product which carbonylation process is conducted in the presence of hydrogen at a molar ratio of hydrogen to carbon monoxide of at least 1 and the catalyst is a zeolite prepared from a synthesis mixture comprising a source of silica, a source of alumina, a source of alkali or alkaline earth metal, water and at least one organic structure directing agent.

In some or all embodiments the present invention provides a zeolite catalyst which provides improved catalytic performance for the carbonylation of dimethyl ether with carbon monoxide in the presence of the catalyst to produce methyl acetate reaction product which carbonylation is carried out in the presence of hydrogen at a molar ratio of hydrogen to carbon monoxide of at least 1 and the zeolite has been prepared from a synthesis mixture comprising a source of silica, a source of alumina, a source of alkali or alkaline earth metal, water and at least one organic structure directing agent.

For the avoidance of doubt, the phrase 'a molar ratio of hydrogen to carbon monoxide of at least 1' means that the molar ratio of hydrogen/carbon monoxide is at least 1.

BRIEF DESCRIPTION OF THE DRAWINGS

The invention is further described with reference to the accompanying drawings, in which:

FIG. 1 depicts the space time yield to methyl acetate in grams per kilogram of catalyst per hour (STY MeOAc g $kg^{-1}$ $h^{-1}$) versus time on stream.

DETAILED DESCRIPTION OF THE INVENTION

The present invention utilises a catalyst which is a zeolite. Zeolites are crystalline aluminosilicates which have framework structures constructed from tetrahedra of $SiO_4$ and $AlO_4$ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The *Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/).

Suitably, zeolites for use in the present invention contain at least one channel or pocket (hereinafter collectively referred to as channels) which is defined by an 8-member ring. Preferably, the 8-member ring channel is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel or pocket is at least 2.5×3.6 Angstroms.

In an embodiment of the present invention, the zeolite is selected from a zeolite of framework type MOR, FER, OFF, CHA, GME and MFS.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite. Examples of zeolites of framework type MFS include ZSM-57.

In an embodiment of the present invention, the zeolite has the framework type MOR and is mordenite, for example mordenite in a hydrogen form or in an ammonium form, preferably mordenite in a hydrogen form.

In addition to the framework elements silicon and aluminium, a zeolite may have additional elements in its framework, for example at least one of gallium, boron and iron, preferably gallium.

In an embodiment of the present invention, the zeolite is mordenite which has, in addition to silicon and aluminium, framework elements selected from at least one of gallium, boron and iron, preferably gallium.

For use in the present invention the catalyst is prepared by crystallizing a zeolite from a synthesis mixture which comprises an organic structure directing agent. Suitably, prior to its use as a catalyst in a carbonylation process the zeolite is treated to remove the organic structure directing agent from the interior of the zeolite. After removal of the organic structure directing agent from the zeolite, the zeolite is preferably composited with a binder material, for example an inorganic oxide, that provides additional hardness to the finished catalyst. The composited mixture can then be extruded to form the desired type of catalyst particle.

For use in the present invention, zeolites, such as mordenite, may be synthesised by the crystallisation of a zeolite from a synthesis mixture comprising a source of silica, a source of alumina, a source of alkali or alkaline earth metal, water and an organic structure directing agent.

A preferred procedure for preparing a zeolite for use in carbonylation processes of the present invention comprises the following steps:

(i) preparing the zeolite from a synthesis mixture which contains an organic structure directing agent;
(ii) treating the zeolite prepared in step (i) to remove the organic structure directing agent from its structure;
(iii) treating the zeolite of step (ii) with an aqueous solution of ammonium ions;
(iv) drying the ammonium treated zeolite; and
(v) treating the zeolite of step (iv) to produce a hydrogen form zeolite.

A synthesised zeolite may have excess cations and anions in the pores or on the surface of the zeolite structure, such as excess sodium and aluminate ions. These can be removed by washing. Thus, suitably, prior to step (ii), the zeolite prepared in step (i) may be washed, for example with water, preferably deionised water. Optionally, a washed zeolite may be dried before treating the zeolite to remove the organic structure directing agent.

Once the zeolite has been synthesised, it can be composited with a binder material.

A preferred procedure for preparing a zeolite composited with a binder for use in carbonylation processes of the present invention further comprises the following steps:

(vi) compositing the zeolite prepared in step (v) with an inorganic oxide binder to form a zeolite composite; and (vii) calcining the zeolite composite.

Optionally, prior to the calcining step (vii), the zeolite composite may be formed into a shaped body.

The sources of the silica, alumina and alkali or alkaline earth metal may be those conventionally used in zeolite synthesis. Representative of silica sources are colloidal silica, precipitated silica, silica gel, fumed silica and solid silica, silicon-containing compounds, such as silicic acid, metal silicates, such as sodium silicate and metallosilicates including aluminosilicates, for example, sodium aluminosilicate.

The source of alumina may be provided by a variety of sources, including activated alumina, alumina trihydrate, gamma alumina, and water soluble aluminium salts, such as aluminium sulphate, aluminium nitrate, hydrated aluminium hydroxides and aluminates, such as sodium aluminate or other metal aluminates.

It will be understood that the silica and alumina utilised in the synthesis mixture for preparing the zeolite can be supplied by one or more initial reagents. For example silica can be supplied by an aqueous solution of sodium hydroxide or an aqueous solution of sodium silicate.

The sources of the alkali or alkaline earth metal include alkali metal or alkaline metal salts readily soluble in water, such as sodium aluminate or sodium silicate or they may be in the form of hydroxides, such as alkali metal hydroxides, preferably, sodium hydroxide.

If additional metals are desired to be present in the framework of the zeolite, such as trivalent metals selected from at least one of gallium, boron and iron, they will generally be added to the synthesis mixture in the form of water soluble salts.

In an embodiment of the invention, the zeolite is prepared from a synthesis mixture which further comprises a source of gallium oxide ($Ga_2O_3$), such as gallium nitrate. In particular, mordenite containing gallium as a framework element is prepared from a synthesis mixture comprising a source of gallium oxide.

Organic structure directing agents are known to be used in zeolite synthesis. The selection of an organic structure directing agent is dependent upon the desired zeolite structure to be achieved. Zeolites for use in the present invention may be synthesised using organic structure directing agents which are basic nitrogen compounds including primary amines, secondary amines, tertiary amines, salts and bases of quaternary ammonium compounds and heterocyclic nitrogen compounds. These compounds may be aliphatic or aromatic.

Suitable amine structure directing agents include tributylamine, diisobutylamine, cyclohexylamine, isobutylamine, cycloheptylamine, triethylamine, tert-octylamine, piperidine and pyrrolidine.

Suitable salts and bases of quaternary ammonium compounds include salts and bases of aliphatic quaternary ammonium compounds, aromatic quaternary ammonium compounds and heterocyclic quaternary ammonium compounds. Suitable compounds include hydroxides and salts, such as halides, for example bromides.

Examples of aliphatic quaternary ammonium structure directing agents include salts of tetraalkylammonium compounds and trialkylmethyl ammonium compounds.

Suitable salts of tetraalkylammonium compounds include those of tetramethylammonium, tetraethylammonium, tetrapropylammonium and tetrabutylammonium compounds, such as tetraethylammonium hydroxide and tetraethylammonium halides, for example tetraethylammonium bromide.

Suitable salts of trialkylmethyl ammonium compounds include those of triethylmethylammonium halides, for example triethylmethylammonium bromide and triethylbutylammonum bromide and trimethylbutylammonium bromide.

Examples of aromatic quaternary ammonium compounds include phenyl or benzyl trialkylammonium compounds, for example benzyl trimethylammonium bromide, benzyl triethyl ammonium bromide and phenyl trimethylammonium bromide or phenyl or benzyl tetraalkyl ammonium compounds.

Examples of heterocyclic quaternary ammonium structure directing agents include salts and bases of ethyl piperidinium and 1,1-diethyl-piperidinium for example 1,1-diethyl-piperidinium hydroxide.

Triquaternary and diquaternary ammonium salts can also be used, for example 1,4 bis(triethylammonium) butane dibromide.

In some or all embodiments of the present invention the organic structure directing agent is selected from tetraethylammonium bromide ($Et_4NBr$), methyl triethylammonium bromide ($Et_3NMeBr$), benzyl trimethylammonium bromide ($PhCH_2NMe_3Br$) and 1,4 bis(triethylammonium)butane dibromide (($Et_3N(CH_2)_4NEt_3)Br_2$).

A preferred organic structure directing agent is tetraethylammonium bromide.

Additional examples of basic nitrogen compounds which may be employed as structure directing agents are heterocyclic compounds which possess at least one amine functional group, for example morpholines, such as morpholine hydrobromide.

One or more basic nitrogen organic structure directing agents may be employed in the synthesis mixture.

Other organic structure directing agents can also be used in the zeolite synthesis mixture, for example $C_1$-$C_4$ alcohols, such as methanol, ethanol, propanols and 1,2 dihydroxyethane.

The components of the synthesis mixture can be added to water in any order.

In some or all embodiments of the present invention a zeolite, for example mordenite, may be prepared from a synthesis mixture which comprises silica, for example fumed silica, a water soluble aluminate, for example sodium aluminate, an alkali metal hydroxide, for example sodium hydroxide, an organic structure directing agent, for example a quaternary ammonium compound, such as an aliphatic quaternary ammonium compound, for example a tetraalkylammonium compound, in particular a tetraethylammonium compound and more particularly a tetraalkylammonium halide, for example tetraethylammonium bromide, water and optionally a source of gallium oxide.

In an embodiment of the present invention, the zeolite is a mordenite which mordenite contains gallium as a framework element and has been prepared from a synthesis mixture comprising fumed silica, sodium hydroxide, sodium aluminate, a source of gallium oxide such as gallium nitrate and tetraethylammonium bromide.

In order to maintain a predetermined composition in the zeolite it will generally be preferable to employ starting materials of known purity and composition so that composition control is maintained.

The components are brought together in defined proportions in water to compose a zeolite-forming aqueous synthesis mixture. The synthesis mixture is hydrothermally treated (with or without pressure) for a time and at a temperature to promote crystallisation.

Suitably, the synthesis mixture is maintained until crystals of the zeolite are formed, for example for a period of from 6 to 500 hours at elevated temperature, for example at a temperature of 80° C. to 210° C. At lower temperatures, for example 80° C., the crystallisation time is longer. Hydrothermal conditions found to be particularly suitable are a temperature of 150° C. to 170° C. for a period of about 3 to 14 days with agitation, for example with stirring, rotation or tumbling.

The crystallisation is performed with or without pressure but is suitably performed under pressure, for example in a stirred or tumbled autoclave. The resulting crystalline zeolite is then separated from the liquid and recovered, for example by filtration, washing with water, suitably with deionised or distilled water and dried. The synthetic zeolite crystallises as a fine powder which exhibits an x-ray diffraction pattern characteristic of that particular type of zeolite.

The proportions of the components of the synthesis mixture can be adjusted to produce the desired zeolite. In the case of mordenite, the following molar ratios, expressed as oxide ratios, of synthesis mixture components may be employed:

$SiO_2/M_2O_3$ from 10 to 100, preferably 20 to 60
$H_2O/Al_2O_3$ from 500 to 3000
$SDA/Al_2O_3$ from 1 to 15
$Na_2O/Al_2O_3$ from 1 to 15, for example 1 to 10 wherein M is a trivalent metal selected from one or more of Al, Ga, B and Fe; SDA is the organic structure directing agent, suitably a basic nitrogen compound.

As a result of the crystallisation process, the recovered zeolite contains within its pores the organic structure directing agent used in the synthesis mixture. The crystalline structure essentially wraps around the organic structure directing agent and the organic structure directing agent is removed so that the zeolite can exhibit catalytic activity.

Prior to its use as a catalyst in the carbonylation processes of the present invention, the organic structure directing agent is removed from within the pores of the zeolite. A variety of removal methods may be used including combustion or by thermal treatment. In general, at least 50% of the organic structure directing agent is removed, and preferably essentially all the organic structure directing agent is removed.

A preferred method of removal is by a thermal treatment, such as by calcining. Calcination conditions include temperatures ranging from about 300° C. to about 650° C., preferably from about 400° C. to about 600° C., for example from about 450° C. to 550° C. Calcination may take place in the presence of an inert atmosphere, such as nitrogen or an oxidising atmosphere such as oxygen or air for a period of time ranging from about 1 to about 9 hours or longer.

In some or all embodiments of the present invention, the organic structure directing agent is removed from the zeolite by calcining the zeolite at a temperature of from about 450° C. to about 550° C., suitably for a duration of from 1 to 12 hours in the presence of air, such as static air.

Preferably the atmosphere is carefully controlled in order to avoid runaway combustion of any carbon remaining on the zeolite after removal of the organic structure directing agent. Such carbon is preferably removed from the zeolite by calcining in air. Preferably, the calcination step is controlled such that the temperature is increased in a controlled manner to the final calcination temperature. Careful control of the increase in temperature prevents or at least minimises local overheating of the zeolite. Controlled calcination to the desired calcination temperature may be effected by applying slow ramp rates, such as less than 10° C./min, preferably less than 5° C./min.

Zeolites containing alkali or alkaline earth metal, typically sodium are preferably treated to reduce the alkali/alkaline earth metal content either before or after treating the zeolite to remove the organic structure directing agent. Preferably, the alkali/alkaline earth metal content is reduced after said removal treatment. Suitable removal treatments include conventional ion exchange procedures with replacing cations. Ion exchange may be carried out one or more times by contacting the zeolite with an aqueous solution containing the replacing cations. In general, ion exchange is conducted at temperatures of from about 25° C. to about 100° C. for a suitable time interval, for example about 1 to 6 hours. The degree of the ion-exchange can be varied by changing the time of the contact, concentration of the replacing cation solution and temperature.

Typical replacing cations include hydrogen, ammonium and metal cations, including mixtures thereof. Of the replacing cations, preference is given to cations of hydrogen, ammonium, Group IB metals, for example copper, Group VIIB metals for example, platinum and Group VIA metals, for example tin and mixtures thereof, generally employed in the form of their salts, preferably the nitrates, chlorides or sulphates. Preferably ion-exchange is conducted with a source of ammonium cations such as an ammonium salt, for example ammonium nitrate or ammonium chloride.

Following contact with an aqueous salt solution of the desired replacing cation, the zeolite may be washed with water and dried to produce a dry zeolite having the replacing cations occupying the alkali/alkaline earth metal sites.

Preferably, zeolites utilised in the present invention are in their hydrogen or ammonium forms, most preferably, in the hydrogen form.

The ammonium form of a zeolite may readily be converted to the hydrogen form by calcining. Calcination is suitably carried out at temperatures in the range 300° C. to 650° C., preferably in the range 400° C. to 550° C. Calcination causes the ammonium ion to decompose, leaving the structure in the hydrogen form.

As-synthesised zeolites are fine crystalline powders. Since a powder has no significant mechanical strength, its practical applications are limited. Mechanical strength can be conferred on a zeolite, such as by forming the zeolite into shaped particles. Processes for forming zeolites into shaped particles are well-known in the art and may be accomplished by forming a gel or paste of the zeolite powder with the addition of a suitable binder such as a clay or an inorganic oxide, and then extruding the gel or paste into the desired shape and then dried. The resultant extrudate may also be calcined, for example at temperatures of at least 500° C., such as in the range 500° C. to 550° C.

Thus, suitably, a zeolite for use in the present invention is composited with at least one binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example, boehemite type alumina.

The relative proportions of the zeolite and the binder material may vary widely but suitably the binder material may be present in a composite in an amount in the range of 10% to 90% by weight of the composite, preferably, in the range of 10% to 65% by weight of the composite.

Zeolite powders may also be formed into particles without the use of a binder. Typical zeolite particles include extrudates whose cross-sections are circular or embrace a plurality of arcuate lobes extending outwardly from the central portion of the zeolite particles.

In an embodiment of the present invention, a zeolite, for example mordenite, is composited with at least one inorganic oxide binder material, which may suitably be selected from aluminas, silicas and alumina-silicates, and is utilised in the form of a shaped body, such as an extrudate. In particular, mordenite is composited with an alumina, for example a boehmite alumina. The mordenite composited with alumina may contain gallium as a framework element.

The silica to alumina molar ratio of the zeolites for use in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as mordenite, may range from as low as 5 to over 90.

The SAR of the zeolites for use in the present invention may suitably be in the range from 10 to 90, for example, 20 to 60, such as 20 to 40. However, if desired, zeolites for use in the present invention may also have a SAR in the range 10 to 22, such as 13 to 22.

A zeolite prepared from a synthesis mixture comprising an organic structure directing agent, and preferably composited with a binder material, is usefully employed in the carbonylation of dimethyl ether with carbon monoxide. Advantageously, such zeolites demonstrate high catalytic activity in carbonylation processes in which an equimolar or excess amount of hydrogen is present.

Thus, the present invention further provides for the use of a zeolite prepared from a synthesis mixture comprising a source of silica, a source of alumina, a source of alkali or alkaline earth metal, water and at least one organic structure directing agent as a catalyst in the carbonylation of dimethyl ether and carbon monoxide in the presence of hydrogen wherein the molar ratio of hydrogen to carbon monoxide is at least 1 to provide improved selectivity and/or productivity to methyl acetate product.

Dimethyl ether employed in the present invention may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the present invention, the dimethyl ether may comprise small amounts of methanol provided that the amount of methanol is not so great as to inhibit the production of methyl acetate reaction product. Suitably, the dimethyl ether may comprise 5 wt % or less, such as 1 wt % or less of methanol.

Diluents may be included in the dimethyl ether. Examples of suitable diluents include nitrogen, argon and helium.

Suitably, the concentration of dimethyl ether is in the range of from 0.1 mol % to 20 mol %, for example 1.5 mol % to 15 mol %, based on the total gaseous feed to the carbonylation process.

Preferably, dimethyl ether is utilised in the carbonylation process in the vapour phase.

As water can inhibit the carbonylation of dimethyl ether to produce methyl acetate, the carbonylation process is preferably carried out under substantially anhydrous conditions. As used herein, "substantially anhydrous conditions" is taken to mean that the concentration of water is less than 1 mol %, preferably less than 0.5 mol %, more preferably less than 0.2 mol %, and most preferably less than 0.1 mol % based on the total gaseous feed to the carbonylation process. Suitably, the dimethyl ether, carbon monoxide, hydrogen and the catalyst are dried prior to use in the carbonylation process.

The carbon monoxide and hydrogen gases utilised in the present invention may be substantially pure, for example, carbon monoxide and hydrogen typically provided by suppliers of industrial gases, or they may contain low levels of impurities that do not interfere with the carbonylation reaction, such as methane and carbon dioxide.

Synthesis gas is a mixture of primarily carbon monoxide and hydrogen in varying amounts but it may also comprise small amounts of carbon dioxide and inert gases and is commercially available. Conventional processes for the production of synthesis gas include conversion reactions of hydrocarbon sources such as steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process may include the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

Suitably, the carbon monoxide and hydrogen utilised in the present invention may be a synthesis gas.

Optionally, the synthesis gas may also comprise one or more of carbon dioxide and inert gases.

The carbonylation process may also be conducted in the presence of a diluent. Examples of suitable diluents include the inert gases, such as nitrogen, argon and helium.

On contact of the carbon monoxide and dimethyl ether with the catalyst under carbonylation reaction conditions, the carbonylation reaction is initiated and methyl acetate is produced as a reaction product. Hydrogen is largely unconsumed in the carbonylation process.

Advantageously, Applicant has found that zeolites prepared using organic structure directing agents perform substantially better than those prepared without the use of organic structure directing agents at start-up and throughout a carbonylation process. Thus, suitably, the molar ratio of hydrogen to carbon monoxide of at least 1 is maintained throughout the process. In particular, the carbonylation process is carried out under hydrogen-rich conditions, which conditions are suitably maintained throughout the process. By hydrogen-rich conditions is meant throughout this specification that the carbonylation process is conducted with a molar excess of hydrogen, such that the molar ratio of hydrogen to carbon monoxide is greater than 1.

In some or all embodiments of the present invention the hydrogen:carbon monoxide molar ratio is in the range 1 to 10, for example 1 to 4 or 1 to 2.

In some or all embodiments of the present invention, the hydrogen:carbon monoxide molar ratio is greater than 1, for example greater than 1 to 4, such as 2 to 4, for instance 2.

Suitably, space time yields (STY) to methyl acetate of from about 100 g·l$^{-1}$ h$^{-1}$ or greater may be achieved in the processes of the present invention, for example STY's of 400 g·l$^{-1}$ h$^{-1}$ or greater, such as in the range 400 g·l$^{-1}$ h$^{-1}$ to 600 g·l$^{-1}$ h$^{-1}$.

Suitably, selectivities to methyl acetate of from about 80% or greater may be achieved in the processes of the present invention, for example a selectivity of 90% or greater, such as in the range 90% to 99%.

In some or all embodiments of the present invention, the carbonylation process is conducted with a hydrogen to carbon monoxide molar ratio of 2 or greater, such as in the range 2 to 4, in the presence of a zeolite catalyst prepared from a synthesis mixture comprising triethylammonium bromide and the selectivity to methyl acetate is at least 85%, for example 90% to 99% and preferably the STY to methyl acetate is at least 400 g·l$^{-1}$ h$^{-1}$, for example in the range 400 g·l$^{-1}$ h$^{-1}$ to 600 g·l$^{-1}$ h$^{-1}$.

To improve selectivity, methyl acetate may be introduced into the process as an additional feed component. Suitably, methyl acetate may be introduced into the process in an amount of from about 0.05 mol % to 5 mol %, for example from about 0.5 mol % to 5 mol % based on the total gaseous feed to the process.

Suitably, the carbonylation process is carried out at a temperature of from about 200° C. to about 350° C., such as from about 240° C. to about 320° C., for example of from about 260° C. to about 300° C., for instance of from about 280° C. to about 300° C.

The carbonylation process may be carried out at a total pressure in the range 1 to 100 barg, such as in the range 10 to 100 barg, for example in the range 20 to 80 barg, preferably in the range 50 to 80 barg.

In an embodiment of the present invention, the carbonylation process is carried out at a temperature of from about 240° C. to about 320° C., for example of from about 280° C. to 300° C. and at a total pressure in the range 10 to 100 barg, for example in the range 60 to 80 barg.

Suitably, the carbonylation process is carried out at a total gas hourly space velocity (GHSV) of from 500 to 40,000 h$^{-1}$, for example from 2000 to 10,000 h$^{-1}$.

Preferably, the carbonylation process is carried out substantially in the absence of halides, such as iodide. By the term 'substantially' is meant that the total halide, for example, iodide content of the gaseous feeds to the process and the catalyst is less than 500 ppm, preferably less than 100 ppm.

If desired, the dimethyl ether, hydrogen and carbon monoxide may be contacted with a guard bed immediately before a bed of catalyst so as to remove impurities therefrom. Suitable guard beds include alumina.

Desirably, the carbonylation process is carried out as a vapour phase process, for example as a fixed bed process. Where the carbonylation process is operated as a vapour phase process, the feedstock(s), prior to entering a reaction zone, may be in the liquid phase. However, prior to contact with the catalyst, it may be desired to volatilize liquid phase components, for example by use of a pre-heater.

The carbonylation process may be carried out in a reaction zone by passing a gaseous feed of dimethyl ether, carbon monoxide and hydrogen, through one or more fixed beds of the catalyst maintained at the desired reaction temperature. It is, of course understood that a reaction zone may be one or more separate reactors with suitable means therebetween to assure that the desired reaction temperature is maintained at the entrance to each reactor.

Prior to use, the catalyst may be activated, for example by heating the catalyst to the desired reaction temperature, and over any desired period of time, under one or more of carbon monoxide, hydrogen and inert gases such as nitrogen and helium.

The reaction product comprises methyl acetate. Typically the reaction product may further comprise additional components such as one or more of unreacted dimethyl ether, unreacted carbon monoxide and hydrogen.

Methyl acetate may be recovered from the reaction product by any suitable means.

Suitably, the reaction product is removed from a reaction zone in the form of a vapour, and thereafter condensed to a liquid fraction comprising the methyl acetate and a non-condensable gas fraction. The gas and liquid fractions may then be separated using known means such as knock-out drums or tangential inlet drums.

The methyl acetate recovered from the reaction product may be sold as such or it may be utilised in downstream chemical processes. For instance, some or all of the recovered methyl acetate may be converted to acetic acid, for example by a hydrolysis process. Hydrolysis processes are known in the art, and include, for example reactive distillation in the presence of an acidic catalyst.

The process may be operated as a continuous or a batch process, preferably as a continuous process.

The invention is now illustrated with reference to the following non-limiting Examples.

EXAMPLES

Example A (Not in Accordance with the Invention)

This Example illustrates the carbonylation of dimethyl ether in the presence of hydrogen and a commercially available H-mordenite made without the use of an organic structure directing agent.

The carbonylation reaction was carried out in a reactor of a pressure flow reactor unit consisting of 16 identical reactors of the type described in WO 2005063372. The reactor (of internal diameter of 9.2 mm) was fitted with an internal tube of diameter 3.2 mm. On a dry mass basis (determined by loss on ignition of the catalyst measured by heating the catalyst from room temperature to 600° C. at a ramp rate of about 30° C. per minute), approximately 2 g (3 ml) of a catalyst was diluted with 3 ml of corundum (particle size 125 to 160 microns) and placed in the reactor on top of a 10 cm bed of corundum (particle size of 125-160 microns). An 11 cm bed of corundum (particle size of 125-160 microns) was placed on top of the catalyst bed. The reactor was pressurised to a total pressure of 70 bar with a 1CO:2H$_2$ gas feed at a flow rate of 12 l/h and then heated at 2° C./min to a temperature of 300° C. and held at this temperature for 3 hours, after which the feed to the reactor was changed to a carbonylation reaction feed of carbon monoxide, hydrogen and dimethyl ether (DME) having a total gas hourly space velocity of 4000 h$^{-1}$ and a molar ratio of H$_2$:CO of 2. The reaction was allowed to run under these conditions for a further 161 hours. The exit stream from the reactor was passed periodically to a gas chromatograph to determine the concentration of reactants and carbonylation products. The catalyst was a H-mordenite (of silica:alumina molar ratio of 20) composited with 20 wt % alumina.

The space time yields of the carbonylation reaction and the selectivities of dimethyl ether to methyl acetate are shown in Tables 1 and 2 respectively below. Space time yield (STY) was calculated as acetic acid equivalents per liter of catalyst per hour. Acetic acid equivalents are determined by multiplying the STY for methyl acetate production by 0.81 [i.e. molecular weight (acetic acid)/molecular weight (methyl acetate)].

Example 1

This Example illustrates the carbonylation of dimethyl ether in the presence of hydrogen and a catalyst prepared with an organic structure directing agent.

Example A was repeated with the catalyst of Example A but wherein the mordenite had been prepared using an organic structure directing agent (tetraethyl ammonium bromide). Prior to use in Example 1, the organic structure directing agent was removed from the pores of the mordenite by calcination.

The space time yields of the carbonylation reaction and the selectivities of dimethyl ether to methyl acetate obtained are shown in Tables 1 and 2 respectively below.

TABLE 1

| Time (hours) | Ex. A Average STY (g. $l^{-1}h^{-1}$) | Ex. 1 Average STY (g. $l^{-1}h^{-1}$) |
| --- | --- | --- |
| 0-20 | 15 | 436 |
| 20-40 | 29 | 440 |
| 40-60 | 32 | 434 |
| 60-80 | 33 | 435 |
| 80-100 | 33 | 439 |
| 100-120 | 34 | 444 |
| 120-140 | 34 | 441 |
| 140-160 | 36 | 450 |

TABLE 2

| Time (hours) | Ex. A Average Selectivity (%) | Ex. 1 Average Selectivity (%) |
| --- | --- | --- |
| 0-20 | 7 | 85 |
| 20-40 | 16 | 91 |
| 40-60 | 20 | 92 |
| 60-80 | 23 | 93 |
| 80-100 | 26 | 93 |
| 100-120 | 28 | 93 |
| 120-140 | 30 | 93 |
| 140-160 | 33 | 94 |

From a comparison of the results shown in Tables 1 and 2, it can clearly be seen that the catalyst prepared without the use of an organic structure directing agent (Ex. A) demonstrates poor catalytic performance in the presence of a molar excess of hydrogen whereas the catalyst which has been prepared with an organic structure directing agent (Ex. 1) provides materially enhanced catalytic performance.

Example 2

Catalyst Preparation

A Ga—Al H-mordenite composited with alumina was prepared in a 4 liter stainless steel autoclave under hydrothermal conditions.

40.5 g NaOH was dissolved in 1080 g of water. 133.6 g $SiO_2$ (fumed silica) was added under vigorous stirring to the NaOH solution. After 1 hour an aqueous solution of tetraethyl ammonium bromide (56.8 g dissolved in 180 g water) was added. After 1 hour an aqueous $Ga(NO_3)_3$ solution (36.12 g of $Ga(NO_3)_3$ hydrate, ex Aldrich dissolved in 210 g water) was added. After 30 minutes an aqueous sodium aluminate solution (3 g of $NaAlO_2$ dissolved in 210 g water) was added. The resultant mixture was stirred for another hour and then transferred in to 4 liter stainless steel autoclave. The hydrothermal treatment conditions were: Temperature=150° C., Reaction Time=14 days with a stirring speed of 200 rpm. After 14 days the precipitate obtained was filtered, washed with deionised water and dried at 110° C. in an air oven. The dried zeolite (silica:alumina molar ratio of 100) was calcined at 550° C. for 12 hours under an atmosphere of static air. The calcined zeolite was ammonium exchanged 3 times by treating 10 ml/g zeolite with 1M $NH_4NO_3$ (aqueous) at 80° C. for 1 hour. The ammonium exchanged zeolite was washed and filtered using deionised water and then dried in an oven at 110° C. to obtain Ga—Al $NH_4$-mordenite. 10 g of the Ga—Al $NH_4$-mordenite and 5 g Pural SCF alumina (ex Sasol) were placed in a powder flask and blended together at 100 r.p.m. for 1 hour at ambient temperature and pressure. The blended mixture was calcined for 3 hours at 500° C. under an atmosphere of static air to form Ga—Al H-mordenite composited with alumina. The zeolite composite was compacted at 12 tonnes in a 32 mm die set using a pneumatic press, and crushed and sieved to a particle size fraction of 100 to 160 microns.

Carbonylation Reaction Procedure

Ga—Al H-mordenite catalyst prepared in accordance with the above was used to catalyse the carbonylation of dimethyl ether with carbon monoxide as follows. The carbonylation reaction was carried out in a pressure flow reactor unit consisting of 16 identical parallel isothermal co-current tubular reactors of the type described in, for example, WO2006107187. 100 microliters (0.0729 g) of the catalyst was loaded onto a metal sinter (20 micrometers pore size) within the reactor. 100 microliters of gamma alumina was placed on top of the catalyst and the remainder of the reactor was filled with carborundum. The catalyst was activated by heating the catalyst at atmospheric pressure at a ramp rate of 5° C./min under a gaseous mixture of carbon monoxide, hydrogen and helium at a molar ratio of 1:2:0.1, at a gas flow rate of 6.1 ml/min to a temperature of 300° C. The reactor was then pressurised to 60 barg and left to equilibrate for two hours at which point catalyst activation was considered complete. The gaseous feed was then replaced by a carbonylation gas feed having a $H_2$:CO molar ratio of about 2 and comprising 58.2 mol % $H_2$, 29 mol % CO, 2.8 mol % He, 5 mol % $CO_2$ and 5 mol % dimethyl ether at a gas flow rate of 6.7 ml/min. The reaction was allowed to continue for 188 hours under these conditions. At 188 hours the carbonylation gas feed was replaced by a gas feed comprising 29 mol % CO, 58.2 mol % nitrogen, 2.8 mol % He, 5 mol % $CO_2$ and 5 mol % dimethyl ether at a gas flow rate of 6.7 ml/min and the reaction continued for a further 100 hours. The exit stream from the reactor was analysed by passing it to an Interscience Trace gas chromatograph equipped with two thermal conductivity detectors (TCD) and one flame ionisation detector (FID): one TCD channel was equipped with two columns, a Carboxen 1010 (2 m*0.32 mm) and a Carboxen 1010 (28 m*0.32 mm). The second TCD channel was equipped with a Poraplot U (2 m*0.32 mm) and a Poraplot Q (12 m*0.32 mm) column. The FID channel was equipped with a Rtx-1,1u (20 m*0.32 mm) and a Rtx-wax, 0.25 u (2 m*0.32 mm) column.

The results of the experiment are shown in FIG. 1 which shows the space time yield to methyl acetate in grams per kilogram of catalyst per hour (STY MeOAc g kg$^{-1}$ h$^{-1}$) versus time on stream. As FIG. 1 shows between 25 hours and 188 hours, a carbonylation gas feed having a molar ratio of $H_2$ to CO of about 2 was used and the MeOAc STY was about 600 g kg$^{-1}$ h$^{-1}$. After 188 hours, the $H_2$ in the gas feed was replaced by $N_2$ and the catalyst started to rapidly deactivate, demonstrating that the presence of $H_2$ in a carbonylation feed is required to achieve high MeOAc space time yields.

Example 3

Preparation of Catalyst A

An aqueous solution of tetraethyl ammonium bromide (56.78 g in 180 g $H_2O$) was added to 133.6 g $SiO_2$ (Aldrich, fumed silica) dispersed in 900 g water and the mixture thoroughly mixed for 1 hour before adding to the mixture, under vigorous stirring, an aqueous NaOH solution (40.64 g dissolved in 180 g $H_2O$). After 90 minutes an aqueous $NaAlO_2$ solution (8.7 g of $NaAlO_2$ (Fischer Scientific GP grade) dissolved in 210 g $H_2O$) and 210 g water were added to the stirred mixture and the mixture stirred for a further hour before being transferred to a 4 L stainless steel autoclave in which it was hydrothermally treated under conditions of a temperature of 150° C. for a period of 3.5 days at a stirring speed of 500 rpm. After 3.5 days zeolite crystals had formed which were separated from the mother liquor by filtration, washed with deionised water and dried at 90° C. in an air oven. 20 g of the dried zeolite (silica:alumina molar ratio of 24) was calcined at 550° C. in static air for 12 hours to remove the organic structure directing agent. The calcined zeolite was subjected to an ammonium exchange procedure by treating it with an aqueous solution of $NH_4NO_3$ (100 mL, 1 M), warmed to 80° C. and the mixture stirred at this temperature for 1 hour. The resultant suspension was filtered and the solid washed with $NH_4NO_3$. This ammonium exchange procedure was repeated twice more. In the final filtration step the solid was washed with deionised water instead of $NH_4NO_3$ before the washed solid was dried in an oven at 90° C. for 24 hours. The dried solid was mordenite in ammonium form. 10 g of the ammonium mordenite and 2.5 g of Pural SCF 55 (Sasol) alumina were gently mixed together until homogenised. Approximately 17 mL of deionised water was added to the homogenised mixture and thoroughly mixed to obtain a homogeneous paste. 4 mL of aqueous $HNO_3$ (6.9 wt. % $HNO_3$ in deionised water) was added to the paste and mixed for 4 hours at room temperature before being dried at 90° C. overnight in an air oven and subsequently calcined in static air for 3 hours at 500° C.

Preparation of Catalyst B

An aqueous solution of methyl triethyl ammonium bromide ($Et_3NMeBr$) (52.96 g in 180 g $H_2O$) was added to 133.7 g $SiO_2$ (Aldrich, fumed silica) dispersed in 900 g water and the mixture thoroughly mixed for 1 hour before adding to the mixture, under vigorous stirring, an aqueous NaOH solution (40.71 g dissolved in 180 g $H_2O$). After 90 minutes an aqueous $NaAlO_2$ solution (17.44 g of $NaAlO_2$ (Fischer Scientific GP grade) dissolved in 210 g $H_2O$) and 210 g water were added to the stirred mixture and the mixture stirred for a further hour before being transferred to a 4 L stainless steel autoclave in which it was hydrothermally treated under conditions of a temperature of 170° C. for a period of 3.5 days at a stirring speed of 550 rpm. After 3.5 days zeolite crystals had formed which were separated from the mother liquor by filtration, washed with deionised water and dried at 90° C. in an air oven. 20 g of the dried zeolite (silica:alumina molar ratio of 13.5) was calcined at 550° C. in static air for 12 hours to remove the organic structure directing agent from the zeolite structure. The calcined zeolite was subjected to an ammonium exchange procedure by treating it with an aqueous solution of $NH_4NO_3$ (200 mL, 1M), warmed to 80° C. and the mixture stirred at this temperature for 1 hour. The resultant suspension was filtered and the solid washed with $NH_4NO_3$. This ammonium exchange procedure was repeated twice more. In the final filtration step the solid was washed with deionised water instead of $NH_4NO_3$ before the washed solid was dried in an oven at 90° C. for 24 hours. The dried solid was mordenite in ammonium form.

17.3 g of the ammonium mordenite and 4.3 g of Pural SCF 55 (Sasol) alumina were gently mixed together until homogenised. 44 mL of deionised water was added to the homogenised mixture and thoroughly mixed to obtain a homogeneous paste. 7 mL of aqueous $HNO_3$ (6.9 wt. % $HNO_3$ in deionised water) was added to the paste and mixed 4 hours at room temperature before being dried at 90° C. overnight in an air oven and subsequently calcined in static air for 3 hours at 450° C.

Carbonylation Reaction Procedure

Each of catalysts A and B prepared above were used to catalyse carbonylation reactions of dimethyl ether with carbon monoxide in the presence of hydrogen. The reactions were carried out in a pressure flow reactor unit consisting of 64 identical parallel isothermal co-current tubular reactors of the type described in, for example WO2006107187. The reactors were arranged in 4 blocks of 16 reactors, each block having an independent temperature control. Each reactor housed a metal sinter having a pore size of 20 micrometers onto which was loaded 100 micro liters of catalyst (pressed and sieved to 100-160 μm fraction) to give a GHSV of 4000 h$^{-1}$. The catalysts were activated by heating at atmospheric pressure to a temperature of 100° C. under an inert gas stream at a flow rate of 6.7 mL/min. per reactor and held at this temperature for 1 hour. The reactors were then pressurised to 70 barg and allowed to equilibrate for one hour at which point catalyst activation was considered complete. A carbonylation reaction feed comprising 29 mol % carbon monoxide, 58 mol % hydrogen, 10 mol % dimethyl ether, 1 mol % $N_2$ and 2 mol % He was introduced into each reactor under reaction conditions of 300° C. and 70 barg and the reaction allowed to continue for 10 days.

The exit stream from a reactor was analysed by passing it to two Interscience Trace gas chromatographs. One gas chromatograph was equipped with one thermal conductivity detector (TCD) having a Molsieve 5A (25 m*0.32 mm) column and one flame ionisation detector (FID) having a DB 624 (28*0.25 mm) column. The second gas chromatograph was equipped with one TCD detector having a Carboxen 1010 (28 m*0.32 mm) column and two FID detectors; a first FID was equipped with a Wax FFAP (18 m*0.25 mm) column and a second FID was equipped with a Gaspro (20 m*25 mm) column.

Table 3 below shows the average acetyls space time yields (STY) and selectivities to methyl acetate achieved for each of Catalysts A and B over the final 100 hours of the carbonylation reaction.

TABLE 3

| Catalyst | OSDA* | STY (g l$^{-1}$h$^{-1}$) | Selectivity (%) |
|---|---|---|---|
| A | Et$_4$NBr | 734 | 95.7 |
| B | Et$_3$NMeBr | 215 | 98.5 |

*OSDA = organic structure directing agent

TABLE 4

| Catalyst | OSDA* | STY (g l$^{-1}$h$^{-1}$) | Selectivity (%) |
|---|---|---|---|
| C | [Et$_3$N(CH$_2$)$_4$NEt$_3$]Br$_2$ | 123 | 96.5 |
| Ex. A | None | 99 | 92.3 |

*OSDA = organic structure directing agent

Example 4

Preparation of Catalyst C

An aqueous solution of 1,4 bis(triethylammonium) butane dibromide [Et$_3$N(CH$_2$)$_4$NEt$_3$]Br$_2$ (51 g in 180 g H$_2$O) was added to 133.5 g SiO$_2$ (Aldrich, fumed silica) dispersed in 900 g water and the mixture thoroughly mixed for 1 hour before adding to the mixture, under vigorous stirring, an aqueous NaOH solution (40.3 g dissolved in 180 g H$_2$O). After 90 minutes an aqueous NaAlO$_2$ solution (17.50 g of NaAlO$_2$ (Fischer Scientific GP grade) dissolved in 210 g H$_2$O) and 210 g water were added to the stirred mixture and the mixture stirred for a further hour before being transferred to a 4 L stainless steel autoclave in which it was hydrothermally treated under conditions of a temperature of 170° C. for a period of 3.5 days at a stirring speed of 550 rpm. After 3.5 days zeolite crystals had formed which were separated from the mother liquor by filtration, washed with deionised water and dried at 110° C. in an air oven. 50 g of the dried zeolite (silica:alumina molar ratio of 13.4) was calcined at 550° C. in static air for 12 hours to remove the organic structure directing agent from the zeolite structure. The calcined zeolite was subjected to an ammonium exchange procedure by treating it with an aqueous solution of NH$_4$NO$_3$ (500 mL, 1M), warmed to 80° C. and the mixture stirred at this temperature for 1 hour. The resultant suspension was filtered and the solid washed with NH$_4$NO$_3$. This ammonium exchange procedure was repeated twice more. In the final filtration step the solid was washed with deionised water instead of NH$_4$NO$_3$ before the washed solid was dried in an oven at 90° C. for 24 hours. The dried solid was mordenite in ammonium form. 30 g of the ammonium mordenite and 7.5 g of Pural SCF 55 (Sasol) alumina were gently mixed together until homogenised. Approximately 50 mL of deionised water was added to the homogenised mixture and thoroughly mixed to obtain a homogeneous paste. 12 mL of aqueous HNO$_3$ (6.9 wt. % HNO$_3$ in deionised water) was added to the paste and mixed for 4 hours at room temperature before being dried at 90° C. overnight in an air oven and subsequently calcined in static air for 3 hours at 450° C.

Carbonylation Reaction Procedure

The catalyst of Example A and catalyst C prepared above were used to catalyse carbonylation reactions of dimethyl ether with carbon monoxide in the presence of hydrogen using the carbonylation reaction procedure described in Example 3 above employing a carbonylation reaction feed comprising 29 mol % carbon monoxide, 58 mol % hydrogen, 10 mol % dimethyl ether, 0.5 mol % methyl acetate, 0.5 mol % N$_2$ and 2 mol % He under reaction conditions of 300° C. and 70 barg for a period of 10 days.

Table 4 below shows the average acetyls space time yields (STY) and selectivities to methyl acetate achieved over the final 100 hours of the carbonylation reaction for each of the catalyst of Example A and catalyst C.

Example 5

Preparation of Catalyst D

An aqueous solution of benzyl trimethylammonium bromide (PhCH$_2$NMe$_3$Br) (61.14 g in 180 g H$_2$O) was added to 133.6 g SiO$_2$ (Aldrich, fumed silica) dispersed in 900 g water and the mixture thoroughly mixed for 1 hour before adding to the mixture, under vigorous stirring, an aqueous NaOH solution (40.64 g dissolved in 180 g H$_2$O). After 90 minutes an aqueous NaAlO$_2$ solution (17.44 g of NaAlO$_2$ (Fischer Scientific GP grade) dissolved in 210 g H$_2$O) and 210 g water were added to the stirred mixture and the mixture stirred for a further hour before being transferred to a 4 L stainless steel autoclave in which it was hydrothermally treated under conditions of a temperature of 170° C. for a period of 3.5 days at a stirring speed of 550 rpm. After 3.5 days zeolite crystals had formed which were separated from the mother liquor by filtration, washed with deionised water and dried at 90° C. in an air oven. 20 g of the dried zeolite (silica:alumina molar ratio of 13.4) was calcined at 550° C. in static air for 12 hours to remove the organic structure directing agent from the zeolite structure. The calcined zeolite was subjected to an ammonium exchange procedure by treating it with an aqueous solution of NH$_4$NO$_3$ (200 mL, 1M), warmed to 80° C. and the mixture stirred at this temperature for 1 hour. The resultant suspension was filtered and the solid washed with NH$_4$NO$_3$. This ammonium exchange procedure was repeated twice more. In the final filtration step the solid was washed with deionised water instead of NH$_4$NO$_3$ before the washed solid was dried in an oven at 90° C. for 24 hours. The dried solid was mordenite in ammonium form.

19.3 g of the ammonium mordenite and 4.8 g of Pural SCF 55 (Sasol) alumina were gently mixed together until homogenised. 43 mL of deionised water was added to the homogenised mixture and thoroughly mixed to obtain a homogeneous paste. 7.7 mL of aqueous HNO$_3$ (6.9 wt. % HNO$_3$ in deionised water) was added to the paste and mixed for 4 hours at room temperature before being dried at 90° C. overnight in an air oven and subsequently calcined in static air for 3 hours at 450° C.

Carbonylation Reaction Procedure

Catalyst D and B prepared above were used to catalyse carbonylation reactions of dimethyl ether with carbon monoxide in the presence of hydrogen using the carbonylation reaction procedure described in Example 3 above employing a carbonylation reaction feed comprising 29 mol % carbon monoxide, 58 mol % hydrogen, 10 mol % dimethyl ether, 1 mol % N$_2$ and 2 mol % He under reaction conditions of 280° C. and 70 barg for a period of 10 days.

Table 5 below shows the average acetyls space time yields (STY) and selectivities to methyl acetate achieved over the final 100 hours of the carbonylation reaction for each of catalyst B and catalyst D.

TABLE 5

| Catalyst | OSDA* | STY (g l⁻¹h⁻¹) | Selectivity (%) |
|---|---|---|---|
| B | Et₃NMeBr | 88 | 98.4 |
| D | PhCH₂NMe₃Br | 64 | 98.2 |

*OSDA = organic structure directing agent

The invention claimed is:

1. A process for the carbonylation of dimethyl ether with carbon monoxide in the presence of a catalyst to produce methyl acetate reaction product which carbonylation process is conducted in the presence of hydrogen at a molar ratio of hydrogen to carbon monoxide of greater than 1 and the catalyst is a mordenite zeolite prepared from a synthesis mixture comprising at least one organic structure directing agent.

2. A process according to claim 1 wherein the synthesis mixture further comprises a source of silica, a source of alumina, a source of alkali or alkaline earth metal and water.

3. A process according to claim 2 wherein the synthesis mixture further comprises a source of gallium oxide ($Ga_2O_3$).

4. A process according to claim 1 wherein the organic structure directing agent is a basic nitrogen compound.

5. A process according to claim 4 wherein the basic nitrogen compound is selected from primary amines, secondary amines, tertiary amines, salts and bases of quaternary ammonium compounds and heterocyclic nitrogen compounds.

6. A process according to claim 5 wherein the quaternary ammonium compound is an aliphatic or aromatic quaternary ammonium compound.

7. A process according to claim 6 wherein the aliphatic quaternary compound is selected from salts of a tetraalkyl ammonium compound and trialkylmethyl ammonium compounds.

8. A process according to claim 7 wherein the tetraalkyl ammonium compound is a tetraethyl ammonium compound.

9. A process according to claim 1 wherein the organic structure directing agent is selected from $Et_4NBr$, $Et_3NMeBr$, $PhCH_2NMe_3Br$ and $(Et_3N(CH_2)_4NEt_3)Br_2$.

10. A process according to claim 9 wherein the organic structure directing agent is $Et_4NBr$.

11. A process according to claim 1 wherein the organic structure directing agent is removed from the zeolite prior to its use as catalyst.

12. A process according to claim 11 wherein the removal of the organic structure directing agent from the zeolite is effected by a thermal treatment.

13. A process according to claim 12 wherein the thermal treatment is calcination carried out at a temperature in the range 450° C. to 550° C.

14. A process according to claim 1 wherein the mordenite is in a hydrogen form.

15. A process according to claim 1 wherein the zeolite has the framework elements silicon, aluminium and at least one of gallium, boron and iron.

16. A process according to claim 15 wherein the zeolite has the framework elements silicon, aluminium and gallium.

17. A process according to claim 1 wherein the zeolite is composited with a binder material.

18. A process according to claim 17 wherein the binder is an alumina.

19. A process according to claim 1 wherein the catalyst is utilised in the form of a shaped body.

20. A process according to claim 1 wherein the molar ratio of hydrogen to carbon monoxide is in the range 2 to 4.

21. A process according to claim 1 wherein the carbon monoxide and hydrogen utilised in the process is a synthesis gas.

22. A process according to claim 1 wherein the process is carried out at a temperature of from 200° C. to 350° C.

23. A process according to claim 1 wherein the process is carried out at a total pressure in the range 10 to 100 barg.

24. A process according to claim 1 wherein water is present at a concentration of less than 1 mol % based on the total gaseous feed to the carbonylation process.

25. A process according to claim 1 wherein methyl acetate is introduced into the process in an amount of from 0.05 mol % to 5 mol % based on the total gaseous feed to the process.

26. A process according to claim 1 wherein the process is carried out as a vapour phase process.

27. A process according to claim 1 wherein methyl acetate is recovered from the methyl acetate reaction product and some or all of the recovered methyl acetate is converted to acetic acid.

28. A process according to claim 1 wherein the process is operated as a continuous process.

29. A process according to claim 1 wherein the zeolite is prepared by a process comprising the steps:
   (i) preparing the zeolite from a synthesis mixture which contains an organic structure directing agent by bringing together components of the synthesis mixture in defined proportions in water to compose a zeolite-forming aqueous synthesis mixture and hydrothermally treating said aqueous synthesis mixture to promote crystallization of the mixture to form a crystalline zeolite; recovering the zeolite from the mixture and drying said zeolite;
   (ii) treating the zeolite prepared in step (i) to remove the organic structure directing agent from its structure;
   (iii) treating the zeolite of step (ii) with an aqueous solution of ammonium ions;
   (iv) drying the ammonium treated zeolite; and
   (v) treating the zeolite of step (iv) to produce a hydrogen form zeolite.

30. A process according to claim 29 which further comprises the steps:
   (vi) compositing the zeolite prepared in step (v) with an inorganic oxide binder to form a zeolite composite; and
   (vii) calcining the zeolite composite.

31. A process according to claim 30 wherein prior to step (vi) the zeolite composite is formed into a shaped body.

32. A process for improving the performance of a mordenite zeolite catalyst in a process for the carbonylation of dimethyl ether with carbon monoxide in the presence of the catalyst to produce methyl acetate reaction product by conducting the carbonylation process in the presence of hydrogen at a molar ratio of hydrogen to carbon monoxide of greater than 1 and the zeolite is prepared from a synthesis mixture comprising at least one organic structure directing agent.

33. A process according to claim 32 wherein the synthesis mixture further comprises a source of silica, a source of alumina, a source of alkali or alkaline earth metal and water.

34. A process according to claim 32 wherein the carbonylation process is carried out under hydrogen rich conditions.

35. A process according to claim 32 wherein the zeolite is prepared by a process comprising the steps: (i) preparing the zeolite from a synthesis mixture which contains an organic structure directing agent by bringing together components of the synthesis mixture in defined proportions in water to compose a zeolite-forming aqueous synthesis mixture and hydrothermally treating said aqueous synthesis mixture to promote crystallization of the mixture to form a crystalline zeolite; recovering the zeolite from the mixture and drying said zeolite; (ii) treating the zeolite prepared in step (i) to remove the organic structure directing agent from its structure; (iii) treating the zeolite of step (ii) with an aqueous solution of ammonium ions; (iv) drying the ammonium treated zeolite; and (v) treating the zeolite of step (iv) to produce a hydrogen form zeolite.

\* \* \* \* \*